(12) United States Patent
Lin (10) Patent No.: US 7,049,465 B2
(45) Date of Patent: May 23, 2006

(54) PROCESS FOR ENERGY RECOVERY IN PROCESSES FOR THE PREPARATION OF AROMATIC CARBOXYLIC ACIDS

(75) Inventor: Robert Lin, Kingsport, TN (US)

(73) Assignee: Eastman Chemical Company, Kinsport, TN (US)

(*) Notice: Subject to any disclaimer, the term of this patent is extended or adjusted under 35 U.S.C. 154(b) by 106 days.

(21) Appl. No.: 10/617,878

(22) Filed: Jul. 10, 2003

(65) Prior Publication Data

US 2005/0010066 A1 Jan. 13, 2005

(51) Int. Cl.
*C07C 51/16* (2006.01)
*C07C 61/29* (2006.01)
*F22D 7/00* (2006.01)

(52) U.S. Cl. ............... 562/414; 562/404; 562/409; 562/412; 562/413; 122/406.1

(58) Field of Classification Search ........... 562/414, 562/404, 409, 412, 413, 408; 122/406.1
See application file for complete search history.

(56) References Cited

U.S. PATENT DOCUMENTS

| | | |
|---|---|---|
| 3,970,696 A | 7/1976 | Shigeyasu et al. |
| 3,996,271 A | 12/1976 | Yokota et al. |
| 4,158,738 A | 6/1979 | Scott et al. |

(Continued)

FOREIGN PATENT DOCUMENTS

| | | |
|---|---|---|
| EP | 0 962 442 A | 12/1999 |
| EP | 0 734 372 B1 | 5/2000 |
| GB | 1 373 230 | 11/1974 |
| JP | 5-213816 A | 8/1993 |
| JP | 11-349523 A | 12/1999 |
| WO | WO 96/11899 A | 4/1996 |
| WO | WO 02/06201 A1 | 1/2002 |
| WO | WO 02/063141 A1 | 8/2002 |

OTHER PUBLICATIONS

Ryans, J.L. and Roper, D.L., *Steam Jet Ejectors*, Process Vacuum System Design and Operation, 1986, pp. 229–260, Ch. 9, McGraw Hill.
Hung, T.C., Shai, T.Y. and Wang, S.K., *A Review of Organic Rankine Cycles for the Recovery of Low–Grade Waste Heat*, Energy, 1997, pp. 661–667, vol. 22, No. 7, Elsevier Science Ltd., Great Britain.
Hung, T.C., *Waste Heat Recovery of Organic Rankine Cycle Using Dry Fluids*, Energy, 2001, pp. 539–553, Elsevier Science Ltd.
Ibrahim, O.M., Klein, S.A., *Absorption Power Cycles*, Energy, 1996, pp. 21–27, vol. 21, No. 1, Elsevier Science Ltd. Great Britain.
U.S. Appl. No. 10/772,819, filed Feb. 2, 2004, Lin.

*Primary Examiner*—Cecilia J. Tsang
*Assistant Examiner*—Taylor Victor Oh
(74) *Attorney, Agent, or Firm*—Steven A. Owen; Bernard J. Graves, Jr.

(57) ABSTRACT

This invention relates to a process for the manufacture of aromatic carboxylic acids by exothermic liquid phase oxidation of an aromatic feedstock. More particularly, this invention relates to the efficient energy recovery of the exotherm produced by the liquid phase oxidation of an aromatic feedstock. An apparatus useful in recovery of energy from the preparation of aromatic carboxylic acids by the exothermic liquid phase reaction of an aromatic feedstock is described where the primary means of energy recovery is by raising moderate pressure steam. This is coupled with a process to recovery low temperature energy using a process commonly known as an organic Rankine cycle and/or a heat pump. The combination of energy recovery methods increases the overall energy recovery and enables the recovery of reaction energy as either thermal energy (steam) or work or a combination of both.

34 Claims, 3 Drawing Sheets

U.S. PATENT DOCUMENTS

| | | |
|---|---|---|
| 4,356,319 A | 10/1982 | Roffia et al. |
| 4,939,297 A | 7/1990 | Browder et al. |
| 5,463,113 A | 10/1995 | Yamamoto et al. |
| 5,510,521 A | 4/1996 | McGehee et al. |
| 5,567,842 A | 10/1996 | Izumisawa et al. |
| 5,612,007 A | 3/1997 | Abrams |
| 5,723,656 A | 3/1998 | Abrams |
| 5,959,140 A | 9/1999 | Okoshi |
| 5,961,942 A | 10/1999 | Turner et al. |
| 6,143,926 A | 11/2000 | Parten |
| 6,504,051 B1 | 1/2003 | Miller, Jr. et al. |

PROCESS FOR ENERGY RECOVERY IN PROCESSES FOR THE PREPARATION OF AROMATIC CARBOXYLIC ACIDS

FIELD OF THE INVENTION

This invention relates to a process for the manufacture of an aromatic carboxylic acid-rich stream by exothermic liquid phase oxidation of an aromatic feedstock. More particularly, this invention relates to the efficient energy recovery of the exotherm produced by the liquid phase oxidation of an aromatic feedstock.

BACKGROUND OF THE INVENTION

Aromatic carboxylic acids, such as terephthalic acid, isophthalic acid, and napthlene dicarboxylic acid are useful chemical compounds and are raw materials in the production of polyesters. In the instance of terephthalic acid, a single manufacturing facility can produce greater than 100,000 metric tons per annum as feedstock for a polyethylene terephthalate (PET) facility.

Terephthalic acid (TPA) can be produced by the high pressure, exothermic oxidation of a suitable aromatic feedstock such as para-xylene. Typically, these oxidations are carried out in a liquid phase using air or alternate sources of molecular oxygen in the presence of a metal catalyst or promotor compound(s). Methods for oxidizing para-xylene and other aromatic compounds such as m-xylene and dimethyinaphthalene are well known in the art. These oxidation reactions will typically produce reaction gases generally comprising oxidation reaction products such as carbon monoxide, carbon dioxide, and methyl bromide. Additionally, if air is used as the oxygen source, the reaction gases may also contain nitrogen and excess oxygen.

Most processes for the production of TPA also employ a low molecular weight carboxylic acid, such as acetic acid, as part of the reaction solvent. Additionally, some water is also present in the oxidation solvent as well as being formed as an oxidation by-product.

Oxidations of this type are generally highly exothermic, and although there are many ways to control the temperature of these reactions, a common and convenient method is to remove the heat by allowing a portion of the solvent to vaporize during the reaction. The combination of the reaction gases and the vaporized solvent is referred to as a gaseous mixture. The gaseous mixture contains a considerable amount of energy.

Because water is formed as an oxidation by-product, at least a portion of the gaseous mixture either as vapor or condensate is usually directed to a separation device, typically a distillation column, to separate the water from the primary solvent (e.g. acetic acid) so that the water concentration in the reactor is not allowed to build up.

SUMMARY OF THE INVENTION

An objective of this invention is to provide a method for efficient and economical recovery of energy that is generated as a result of a highly exothermic oxidation reaction producing an aromatic carboxylic acid. Another objective of this invention is to provide for the energy recovery while simultaneously performing a chemical separation between a low molecular weight carboxylic acid solvent and water.

In one embodiment of this invention, a process for recovery of thermal energy from an offgas stream is provided the process comprises the following steps:

a) oxidizing an aromatic feedstock with a liquid phase reaction mixture in a reaction zone to form an aromatic carboxylic acid-rich stream and a gaseous mixture;

b) removing in a separation zone a substantial portion of a solvent from the gaseous mixture to form the offgas stream and a solvent rich stream; and c) recovering the thermal energy from at least a portion of the offgas stream in a heat recovery zone; wherein a portion of the offgas stream is condensed to form a condensed mixture; wherein the condensed mixture is optionally recycled back to the separation zone; wherein a portion of the thermal energy is recovered in a working fluid; and wherein a portion of the enthalpy in the working fluid is recovered in a power cycle; wherein the working fluid is a compound or mixture of compounds that have a normal boiling point between about $-100°$ C. to about $90°$ C.

In another embodiment of this invention, a process for recovery of thermal energy from an offgas stream is provided, the process comprises the following steps:

a) removing in a separation zone a substantial portion of an oxidation solvent from a gaseous mixture to form an offgas stream; and b) optionally, recovering thermal energy from a portion of the offgas stream in a first heat recovery device to produce a low pressure steam.

c) recovering thermal energy from a portion of the offgas stream in a second heat recovery device utilizing a working fluid through a power cycle; wherein a portion of the enthalpy in the working fluid is recovered in a power cycle; wherein the working fluid is a compound or mixture of compounds that have a normal boiling point between about $-100°$ C. to about $90°$ C.; and d) optionally, recovering thermal energy from a portion of the offgas stream in a third heat recovery device.

In yet another embodiment of this invention a process for recovery of thermal energy from an offgas stream is provided. The process comprises the following steps:

a) oxidizing an aromatic feedstock with a liquid phase reaction mixture in a reaction zone to form an aromatic carboxylic acid stream and a gaseous mixture;

b) removing in a separation zone a substantial portion of a solvent from the gaseous mixture to form an offgas stream; and c) optionally, recovering thermal energy from a portion of the offgas stream in a first heat recovery device to produce a low pressure steam;

d) recovering thermal energy from a portion of the offgas stream in a second heat recovery device using a working fluid through a power cycle; wherein said working fluid is a compound or mixture of compounds that have a normal boiling point between about $-100°$ C. to about $90°$ C.; and e) optionally, recovering thermal energy from a portion of the offgas stream in a third heat recovery device.

In yet another embodiment of this invention a process for recovery of thermal energy from an offgas stream is provided. The process comprises the following steps in the order named:

a) oxidizing an aromatic feedstock with a liquid phase reaction mixture in a reaction zone to form an aromatic carboxylic acid stream and a gaseous mixture;

b) removing in a separation zone a substantial portion of solvent from the gaseous mixture to form an offgas stream;

c) recovering thermal energy from a portion of the offgas stream in a first heat recovery device to produce a low pressure steam;

d) recovering thermal energy from a portion of the offgas stream in a second heat recovery device using a working fluid through a power cycle; wherein said working fluid is a compound or mixture of compounds that have a normal boiling point between about −100° C. to about 90° C.; and e) recovering thermal energy from a portion of the offgas stream in a third heat recovery device.

DETAILED DESCRIPTION OF THE INVENTION

Figure 1:
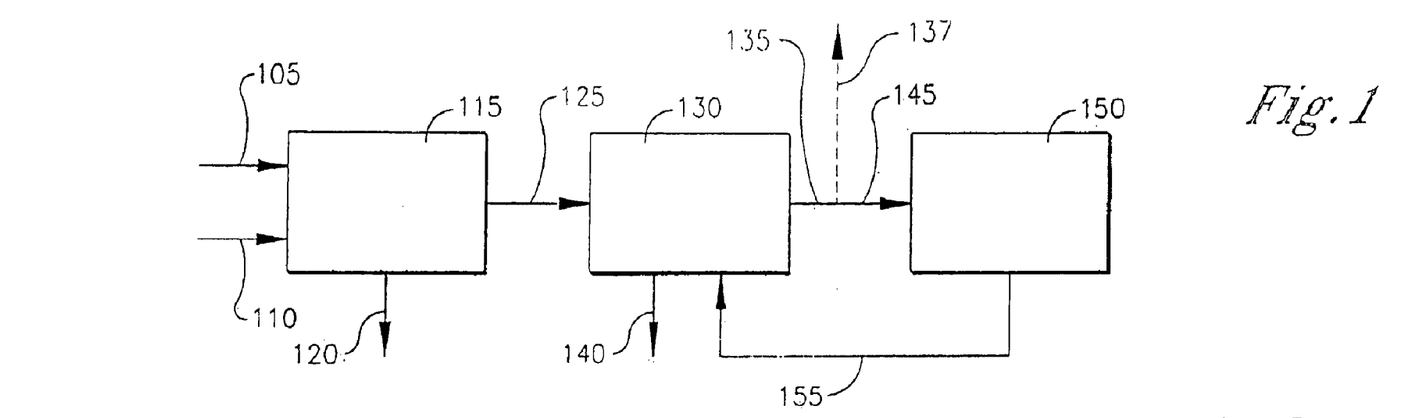
FIG. 1 illustrates different embodiments of the invention where a process to produce thermal energy from an offgas stream is provided.

In the first embodiment of this invention, a process for recovery of thermal energy from an offgas stream 145 is provided in FIG. 1. The process comprises the following steps.

Step (a) comprises oxidizing an aromatic feedstock 105 with a liquid phase reaction mixture 110 in a reaction zone 115 to form an aromatic carboxylic acid-rich stream 120 and a gaseous mixture 125.

The liquid phase reaction mixture 110 comprises water, a solvent, a metal oxidation catalyst and a source of molecular oxygen. The reaction zone 115 comprises at least one oxidation reactor. The oxidizing is completed under reaction conditions which produce the aromatic carboxylic acid-rich stream 120 and the gaseous mixture 125. Typically, the aromatic carboxylic acid-rich stream 120 is a crude terephthalic acid slurry.

Crude terephthalic acid is conventionally made via the liquid phase air oxidation of paraxylene in the presence of a heavy metal oxidation catalyst. Suitable catalysts include, but are not limited to, cobalt, manganese and bromide compounds, which are soluble in the selected solvent. Suitable solvents include, but are not limited to, aliphatic mono-carboxylic acids, preferably containing 2 to 6 carbon atoms, or benzoic acid and mixtures thereof and mixtures of these compounds with water. Preferably the solvent is acetic acid mixed with water, in a ratio of about 5:1 to about 25:1, preferably between about 10:1 and about 15:1. However, it should be appreciated that other suitable solvents, such as those disclosed herein, may also be utilized. Conduit 125 contains a gaseous mixture which comprises vaporized solvent, gaseous by-products, nitrogen and unreacted nitrogen generated as a result of an exothermic liquid phase oxidation reaction of an aromatic to an aromatic carboxylic acid. Patents disclosing the production of terephthalic acid such as U.S. Pat. Nos. 4,158,738 and 3,996,271 are hereby incorporated by reference.

Step (b) comprises removing in a separation zone 130 a substantial portion of a solvent from the gaseous mixture 125 to form the offgas stream 135 and a solvent rich stream 140.

The offgas stream 135 comprises water, gaseous by-products, and small amounts of solvent. When the solvent is a low molecular weight carboxylic acid solvent, the ratio of water to low molecular weight carboxylic acid solvent is in the range of about 80:20 to about 99.99:0.01 by mass. The gaseous by-products comprise oxygen, oxidation by-products, such as, carbon monoxide and carbon monoxide, and in the instance when air is used as a source of molecular oxygen, nitrogen. At least a portion of the offgas stream 135 or all of the offgas stream 135 is sent on to a heat recovery zone via conduit 145.

Typically, the temperature and pressure conditions of the offgas stream 145 are in the range of about 130 to about 220° C. and about 3.5 to about 18 barg. Preferably, the temperature and pressure conditions of the offgas stream 145 are in the range of about 90 to about 200° C. and about 4 to about 15 barg. Most preferably, the temperature and pressure conditions of the offgas stream 145 are in the range of about 130 to about 180° C. and about 4 to about 10 barg.

The gaseous mixture in conduit 125 is directed to the separation zone 130. Typically, the separation zone 130 comprises a high pressure distillation column having between about 20 and about 50 theoretical stages and a condenser or plurality of condensers. In the separation zone 130, the solvent rich stream is recovered via conduit 140. The purpose of the separation zone 130 is to perform a separation wherein at least a portion of the solvent is recovered and excess water is removed. In general, for the purposes of optimized energy recovery, there should be minimal pressure reduction between the contents of conduit 125 and conduit 135 and 145 since this represents a loss of potentially recoverable energy. Therefore, the separation zone 130 should operate at temperature and pressure conditions at or near that of the gaseous mixture from conduit 125. At least a portion or all of the offgas stream 135 is sent to a heat recovery zone via conduit 145, and the rest of the offgas stream 137 can be utilized elsewhere within the process for producing the aromatic carboxylic acid.

Step (c) comprises recovering the thermal energy from at least a portion of the offgas stream 145 in a heat recovery zone 150. In the heat recovery zone 150, a portion of the offgas stream 145 is condensed to form a condensed mixture 155; and the condensed mixture 155 can be optionally recycled back to the separation zone. A working fluid is utilized to recover the thermal energy. Generally the working fluid is a compound or mixture of compounds that have a normal boiling point between about −100° C. to about 90° C.

The recovering of the thermal energy from the offgas stream 145 in a heat recovery zone 150 can be accomplished by any means known in the art. However, generally a power cycle is used. Power cycles are well known in the art. A power cycle is a cycle that takes heat and uses it to do work on the surroundings. There are numerous power cycles that are well known in the art. Examples of power cycles include, but are not limited to, an organic rankine cycle (ORC), a kalina cycle, or a power cycle as described in WO02/063141.

Other examples of power cycles that can be used are disclosed in "A Review of Organic Rankine Cycles (ORCs) for the Recovery of Low-Grade Waste Heat" Energy, Vol. 22, No. 7, pp 661–667,1997, Elsevier Science Ltd, Great Britian and Absorption Power Cycles", Energy, Vol. 21, No. 1, pp 21–27, 1996, Elsevier Science Ltd, Great Britain, are herein incorporated by reference.

One common feature among these examples is the use of low temperature evaporating working fluids. Typically, low temperature evaporating working fluids are used in power cycles to recover thermal energy at relatively low temperatures (e.g. at temperatures generally below 150° C.) instead of water or steam due to the higher power recovery efficiencies. One such cycle is a rankine cycle that is characterized by an isothermal boiling/condensing process. Steam turbine plants usually closely approximate a rankine cycle process wherein the working fluid is substantially water. However, as commonly accepted, rankine cycle power recovery using water/steam at low temperatures (e.g. at temperatures generally below 150° C.) are generally inefficient.

The working fluid can be any fluid as long as it is substantially free of water wherein substantially free is approximately less than 20% by weight. In another embodiment of the invention wherein the working fluid is a compound or mixture of compounds that have a normal boiling point between about −100° C. to about 90° C. Another range is the working fluid can be a compound or mixture of compounds that have a normal boiling point between about −100° C. to about 600° C.

In another embodiment of the invention the working fluid is selected from the group consisting of propane, isopropane, isobutane, butane, isopentane, n-pentane, ammonia, R134a, R11, R12, and a mixtures thereof. R134a, R11, R12 are known in the art and commonly available commercial refrigerants.

Figure 2:
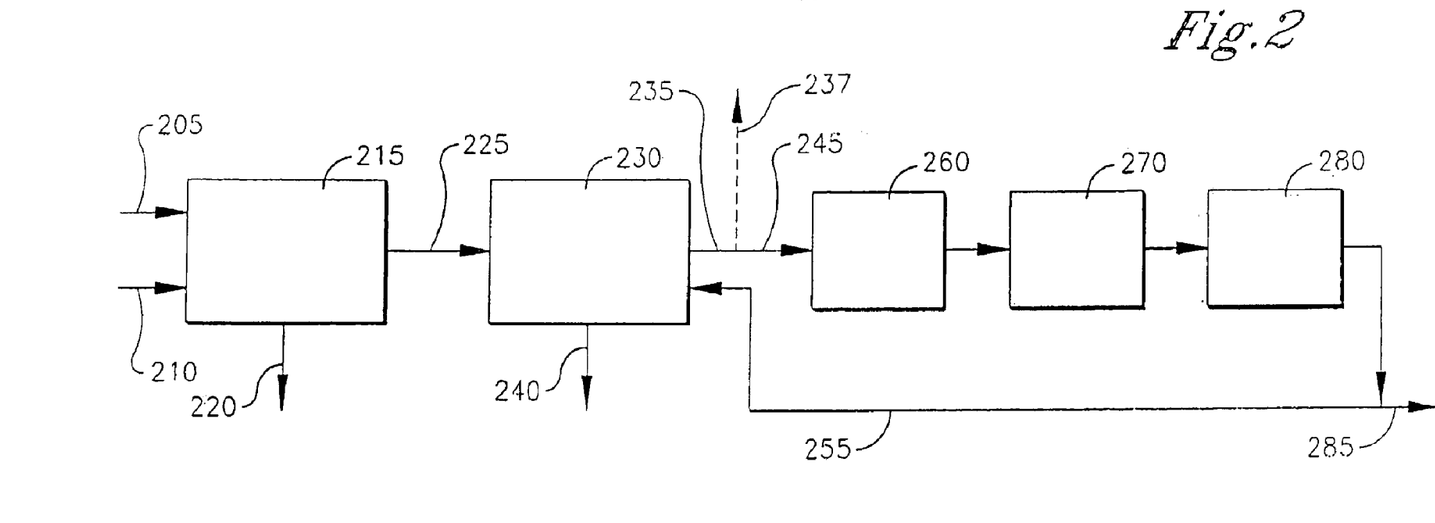
FIG. 2 illustrates different embodiments of the invention where a process to produce thermal energy from an offgas stream is provided through the use of at least one device.

In a second embodiment of the invention, a process for recovering of thermal energy from at least a portion of an offgas stream 235 via conduit 245 is provided in FIG. 2. The process comprises the following steps.

Step (a) removing in a separation zone 230 a substantial portion of a solvent from the gaseous mixture 225 to form the offgas stream 235 and a solvent rich stream 240.

Step (a) in the second embodiment is substantially the same as step (b) in the first embodiment of the invention. In the case where the separation zone comprises a distillation column, the offgas stream 245 exits the top of the distillation column through conduits 245 and 237. The offgas stream 245 comprises gaseous reaction by-products, nitrogen, unreacted oxygen. The solvent, typically acetic acid and water are also present in amounts at or near saturation conditions. The ratio of water to acetic acid is roughly in the range of 80:20 to 99.99:0.01 by mass, preferably in the range of 99.5:0.5 to 98.5:1.5 by mass. A portion of this offgas stream, represented by the contents of conduit 245, can be passed through a series of heat recovery zones, 260, 270, and 280. A portion of the offgas stream 145 is condensed and directed via conduit 255 either as reflux flow to the distillation column in the separation zone 230 via conduit 255 or as liquid distillate via conduit 285.

From a distillation perspective, the role of 260, 270, and 280 is to condense enough material from the overhead offgas stream 245 to provide the distillation column in the separation zone 230 with adequate reflux to drive the solvent and water separation. However, the heat duty necessary to perform the condensation also serves to remove heat generated by the oxidation reaction of the aromatic feedstock to the aromatic carboxylic acid.

It would be useful and efficient to recover the energy. One barrier to efficient energy recovery is due to the presence of non-condensable gases in conduits 245 and 237. The non-condensable gases, for example, nitrogen, oxygen, carbon monoxide, and carbon dioxide, give rise to a condensation heat curve that is not amenable to producing steam.

Figure 3:
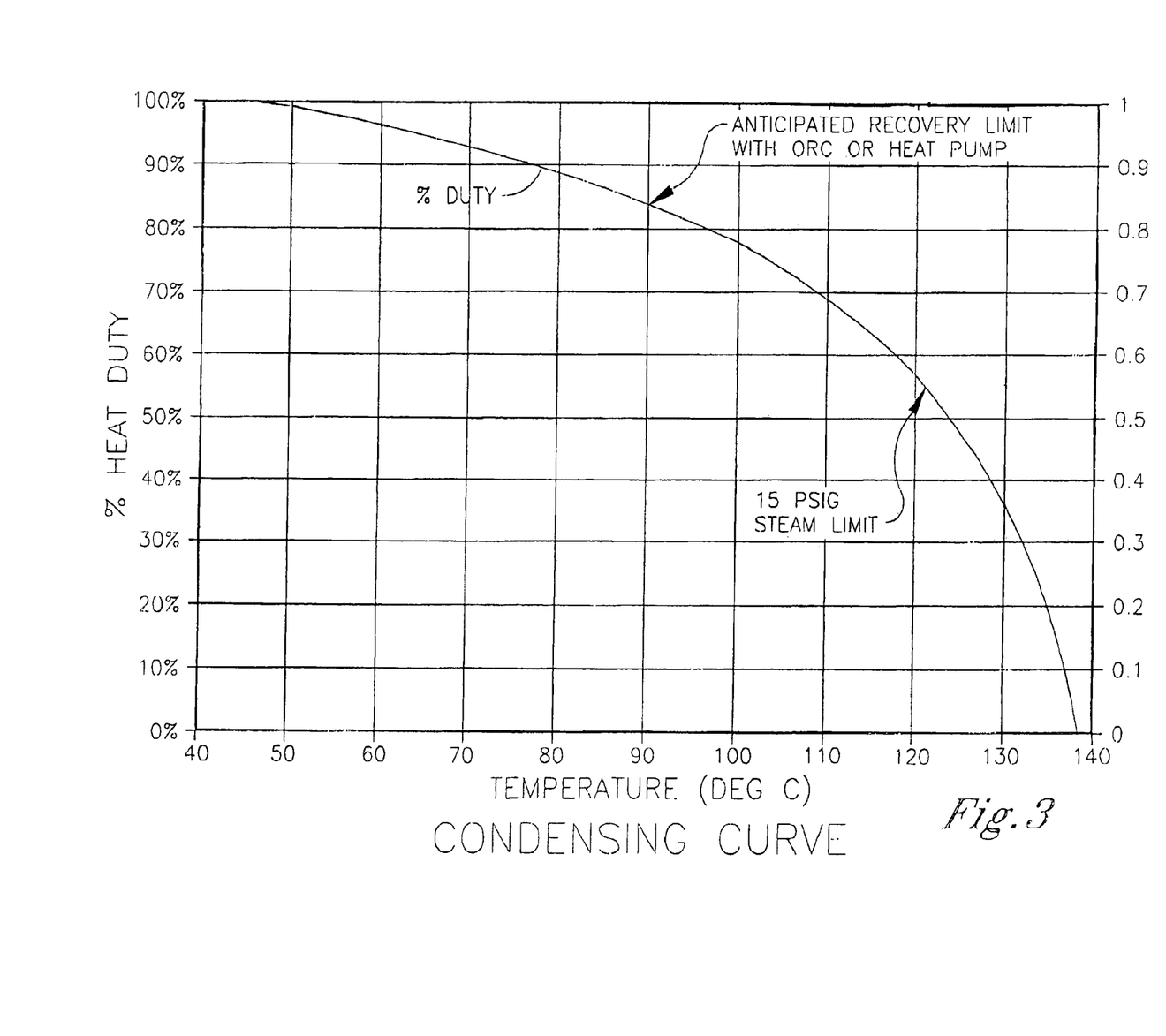
FIG. 3 shows a typical "condensation curve" which describes the heat duty of a condenser or partial condenser as a function of temperature

This is illustrated by the example in FIG. 3. FIG. 3 shows a typical "condensation curve" which describes the heat duty of a condenser or partial condenser as a function of temperature. In this case, the condenser is a partial condenser with a vapor inlet temperature of about 139° C. and an outlet temperature of about 45° C.

If it is desirable to produce about 15 psig steam or about 1 barg in a single partial condenser unit, then FIG. 3 indicates that only 55% of the total duty of the condenser can be used to produce 15 psig steam. This is because 15 psig steam has a saturation temperature of about 121° C. In this example of a partial condenser only 55% of the total duty can be transferred to the steam at temperatures at or above 121° C. This illustrates what is commonly known in heat transfer technology as a temperature "pinch" and represents a thermodynamic limitation on the system.

It is possible to recover more heat if the pressure (and temperature) of the steam generated is lowered. However, this is of limited value because in order to utilize the steam for heating purposes elsewhere within the carboxylic acid production process, the steam must be of sufficient temperature.

Step (b) comprises optionally recovering thermal energy from a portion of the offgas stream 245 in a first heat recovery zone 260 to produce a low pressure steam;

Step (c) comprises recovering thermal energy from a portion of the offgas stream 245 in a second heat recovery zone 270 using a working fluid through a power cycle; wherein said working fluid is a compound or mixture of compounds that have a normal boiling point between about −100° C. to about 90° C.

Step (d) comprises recovering thermal energy from a portion of the offgas stream 245 in a third heat recovery zone 280.

The purpose of step (b), step (c) and step (d)'s is for the efficient recovery of thermal energy. The heat recovery zones 260, 270, and 280 comprise at least one device wherein thermal energy from the offgas stream 145, is recovered. The first heat recovery zone 260 comprises a heat recovery device or plurality of devices wherein the heat transfer is accomplished at a temperature greater than about 121° C. The second heat recovery zone 270 comprises a heat recovery device or plurality of devices wherein the heat transfer is accomplished about a temperature greater than 90° C. The third heat recovery zone 280 comprises a heat device or plurality of devices wherein the heat transfer is accomplished at a temperature greater than 25° C. The heat recovery devices can be any device known in the art.

The relevance of the heat recovery temperatures is evident in the efficiency and usefulness of the heat recovered at those temperatures. For temperatures greater than about 121° C., it is possible to produce about 15 psig (about 1 barg) saturated steam that is useful in industrial applications, such as the manufacture of aromatic carboxylic acids, as a heat media. Although it is possible to produce greater amounts of steam at lower temperatures, the usefulness of such steam is limited. Further, utilization of steam as a heating media for transferring heat to a lower temperature fluid is extremely thermodynamically efficient.

The first heat recovery zone 260 typically comprises, but not limited to a partial condenser.

The second heat recovery zone 270 typically comprises, but not limited to, a heat transfer device such as a condenser or partial condenser transferring heat to a "working fluid", usually a refrigerant compound or a hydrocarbon or mixture of hydrocarbons. For heat and energy recovery at temperatures near or greater than 90° C., several methods are known in the art.

The working fluid can be any fluid as long as it is substantially free of water wherein substantially free is approximately less than 20% by weight. In another embodiment of the invention wherein the working fluid is a compound or mixture of compounds that have a normal boiling point between about −100° C. to about 90° C. Another range is the working fluid can be a compound or mixture of compounds that have a normal boiling point between about −100° C. to about 600° C.

In another embodiment of the invention the working fluid is selected from the group consisting of propane, isopropane, isobutane, butane, isopentane, n-pentane, ammonia, R134a, R11, R12, and a mixtures thereof. R134a, R11, R12 are known in the art and commonly available commercial refrigerants.

Examples of power cycles include, but are not limited to, an organic rankine cycle, a kalina cycle, or a power cycle as described in WO02/063141.

The organic rankine cycle (ORC) which been shown to be effective and economical for recovery of mechanical work and/or electricity from industrial waste heat. Practically, due to the irreversibility of thermodynamic systems, it is impossible to convert all the available thermal energy into useful work. However, due to the limited usefulness of the low pressure steam, it is far more economically advantageous to recover the energy by some other means than raising steam.

There are several examples of industrial processes that utilize an ORC system for energy recovery. The main advantage of the ORC is its superior ability in recovering waste heat with low to medium temperature. For ORC systems where recovering energy in the range of 90 to 120° C., the system has efficiencies in the range of 3 to 20%. System efficiency is defined as the total work derived from the ORC system divided by the total inlet waste heat. The primary factors in the determining system efficiency are the working temperatures for the waste heat stream, the condenser temperature and the thermodynamic properties of the working fluid.

Alternatively, the second heat recovery zone 270 can serve to transfer heater to a heat pump system. A large number of heat pump systems are known in the art. Therefore, any system capable of efficient recovery of energy from low temperature heat is applicable.

The third heat recovery zone 280 comprises a heat recovery device or plurality of devices wherein the heat transfer is accomplished at or near a temperature greater than 25° C. Typically, the third heat recovery zone 280 comprises a water or air-cooled condenser or partial condenser.

In a third embodiment of the invention, a process for recovery of thermal energy from an offgas stream 235 is provided in FIG. 2. The process comprises the following steps.

Step (a) comprises oxidizing an aromatic feedstock 205 with a liquid phase reaction mixture 210 in a reaction zone 215 to form an aromatic carboxylic acid-rich stream 220 and a gaseous mixture 225.

Step (a) in the third embodiment of this invention is the same as step (a) in the first embodiment.

Step (b) comprises removing in a separation zone 230 a substantial portion of a solvent from the gaseous mixture 225 to form the offgas stream 235 and a solvent rich stream 240.

Step (b) in the third embodiment is substantially the same as step (b) in the first embodiment of the invention.

Step (c) comprises optionally recovering thermal energy from a portion of the offgas stream 245 in a first heat recovery zone 260 to produce a low pressure steam;

Step (d) comprises recovering thermal energy from a portion of the offgas stream 245 in a second heat recovery zone 270 using a working fluid in a power cycle; wherein said working fluid is a compound or mixture of compounds that have a normal boiling point between about −100° C. to about 90° C.;

Step (e) comprises recovering thermal energy from at least a portion of the offgas stream 245 in a third heat recovery zone 280.

Step (c), Step (d) and Step (e) in the third embodiment of the invention is substantially the same as Step (b), Step (c) and Step (d) respectively in the second embodiment of this invention.

EXAMPLE

This invention can be further illustrated by the following example of preferred embodiments thereof, although it will be understood that this example is included merely for purposes of illustration and are not intended to limit the scope of the invention unless otherwise specifically indicated.

Figure 4:
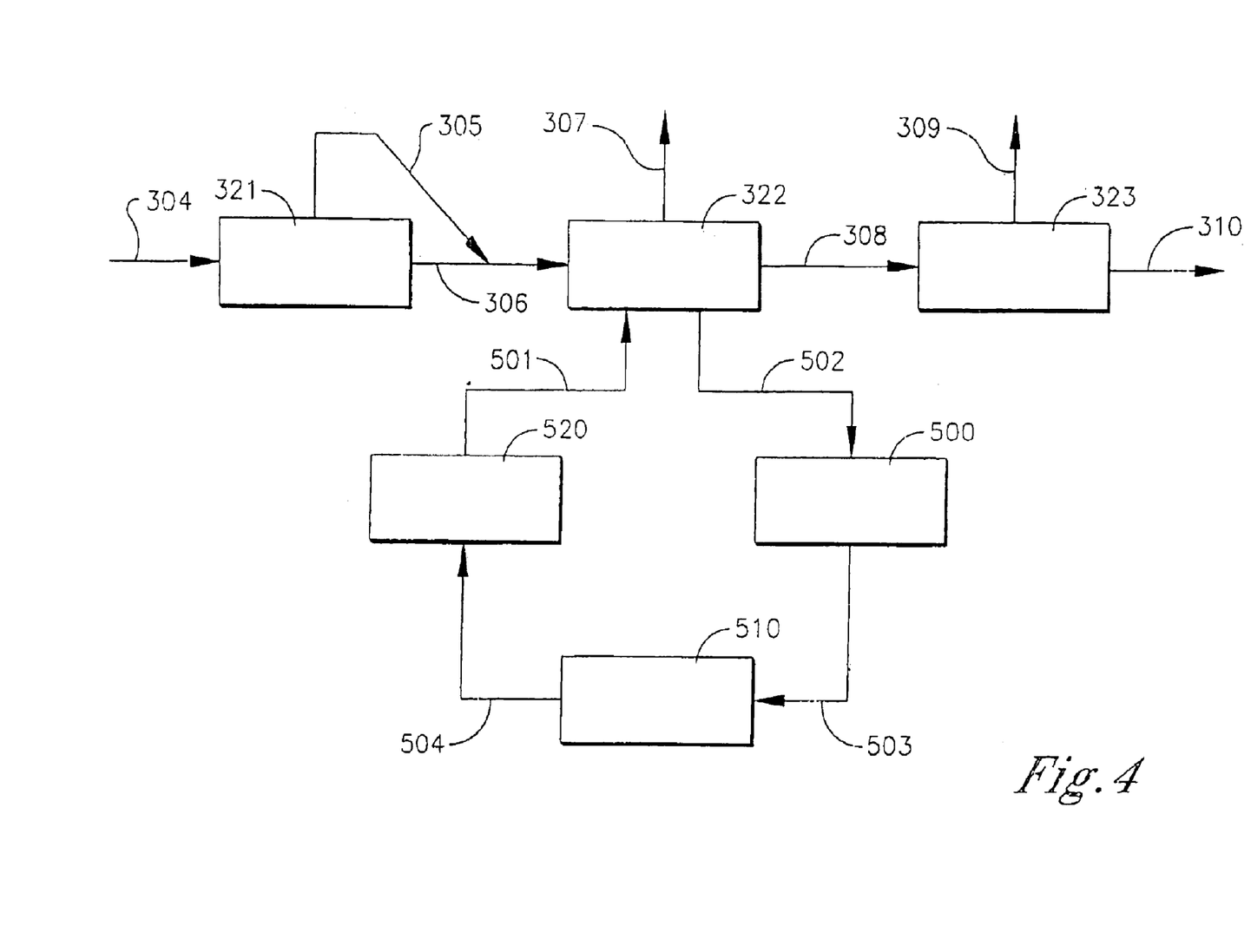
FIG. 4 shows an example of a power recovery system.

FIG. 4 shows an example of a power recovery system. The temperature and pressures are consistent with a terephthaic acid production. In this system, the working fluid for the organic rankine cycle system is n-pentane. Results based on ASPEN Plus™ computer simulation are shown in Table 2. Specific details about the equipment use in the model are shown in Table 1. Note that in this example about 55% of the total duty is used to produce 15 psig steam. An additional 38% of the total duty employs an ORC system for enhanced energy recovery. The overall thermal efficiency of the ORC system is roughly about 7.3%. It is assumed that significant improvements can be made by optimizing the choice of "working fluid" and by optimizing temperature and pressure operating conditions of the ORC system.

TABLE 1

| Item | Description | Comment |
|---|---|---|
| 321 | 15 psig steam generator | Duty~2.18 × $10^6$ BTU/hr |
| 322 | Pentane evaporator | Duty~1.53 × $10^6$ BTU/hr |
| 323 | Heat Exchanger | Duty~0.24 × $10^6$ BTU/hr |
| 500 | Turbine | Work Generated~44 hp |
| 510 | Condenser | Duty~1.41 × $10^6$ BTU/hr |
| 520 | Pump | Work Required~1.4 hp |

TABLE 2

| Stream Name | 304 | 305 | 306 | 307 | 308 | 309 | 310 | 501 | 502 | 503 | 504 |
|---|---|---|---|---|---|---|---|---|---|---|---|
| Mass Flow lb/hr | | | | | | | | | | | |
| NITROGEN | 5919 | 5908 | 11 | 5886 | 33 | 0 | 33 | 0 | 0 | 0 | 0 |
| OXYGEN | 270 | 269 | 1 | 267 | 3 | 0 | 3 | 0 | 0 | 0 | 0 |

TABLE 2-continued

| Stream Name | 304 | 305 | 306 | 307 | 308 | 309 | 310 | 501 | 502 | 503 | 504 |
|---|---|---|---|---|---|---|---|---|---|---|---|
| WATER | 3764 | 1551 | 2213 | 322 | 3442 | 0 | 3442 | 0 | 0 | 0 | 0 |
| HOAC | 47 | 19 | 28 | 6 | 41 | 0 | 41 | 0 | 0 | 0 | 0 |
| PENTANE | 0 | 0 | 0 | 0 | 0 | 0 | 0 | 8400 | 8400 | 8400 | 8400 |
| Total Flow lb/hr | 10000 | 7748 | 2252 | 6481 | 3519 | 0 | 3519 | 8400 | 8400 | 8400 | 8400 |
| Temperature C. | 150.0 | 130.0 | 130.0 | 90.0 | 90.0 |  | 50.0 | 35.0 | 73.2 | 52.7 | 34.6 |
| Pressure psi | 145.2 | 144.2 | 144.2 | 143.2 | 143.2 | 141.2 | 141.2 | 44.3 | 43.3 | 15.0 | 14.0 |
| Vapor Frac | 1 | 1 | 0 | 1 | 0 | 0 | 0 | 0 | 1 | 1 | 0 |
| Liquid Frac | 0 | 0 | 1 | 0 | 1 |  | 1 | 1 | 0 | 0 | 1 |

What is claimed is:

1. A process for recovery of thermal energy from an offgas stream produced in the manufacture of an aromatic carboxylic acid comprising:
   a) oxidizing an aromatic feedstock with a liquid phase reaction mixture in a reaction zone to form an aromatic carboxylic acid-rich stream and a gaseous mixture;
   b) removing in a separation zone at least a portion of a solvent from said gaseous mixture to form said offgas stream and a solvent rich stream; and
   c) recovering said thermal energy from at least a portion of said offgas stream in a heat recovery zone; wherein a portion of said offgas stream is condensed to form a condensed mixture; wherein said condensed mixture is optionally recycled back to said seperation zone; wherein a portion of said thermal energy is recovered in a working fluid; wherein a portion of the enthalpy in said working fluid is recovered in a power cycle comprising an organic rankine cycle or a kalina cycle; and wherein said working fluid is a compound or mixture of compounds that have a normal boiling point between about −100° C. to about 90° C.

2. A process according to claim 1 wherein a portion of said thermal energy from said offgas stream is used to produce steam.

3. A process according to claim 1 wherein said working fluid is selected from the group consisting of propane, isopropane, isobutane, butane, isopentane, n-pentane, ammonia, R134a, R11, R12, and mixtures thereof.

4. A process according to claim 2 wherein said working fluid is selected from the group consisting of propane, isopropane, isobutane, butane, isopentane, n-pentane, ammonia, R134a, R11, R12, and mixtures thereof.

5. A process according to claim 4 wherein said separation zone comprises a distillation column.

6. A process according to claim 5 where said distillation column is operated at a temperature of about 130° C. to about 220° C.

7. A process according to claim 6 wherein said distillation column is operated at a pressure of about 3.5 barg to about 15 barg.

8. A process according to claim 1 wherein said power cycle is an organic rankine cycle.

9. A process for recovery of thermal energy from an offgas streamsaid process comprising the following steps:
   a) removing in a separation zone at least a portion of a solvent from a gaseous mixture to form said offgas stream and a solvent rich stream; and
   b) optionally, recovering thermal energy from a portion of said offgas stream in a first heat recovery zone to produce a low pressure steam
   c) recovering thermal energy from a portion of said offgas stream in a second heat recovery zone utilizing a working fluid; wherein a portion of the enthalpy in said working fluid is recovered in a power cycle comprising an organic rankine cycle or a kalina cycle; wherein said working fluid is a compound or mixture of compounds that have a normal boiling point between about −100° C. to about 90° C.; and
   d) optionally, recovering thermal energy from a portion of said offgas stream in a third heat recovery zone.

10. A process according to claim 9 wherein said power cycle is an organic rankine cycle.

11. A process according to claim 9 wherein said working fluid is selected from the group consisting of propane, isopropane, isobutane, butane, isopentane, n-pentane, ammonia, R134a, R11, R12, and mixtures thereof.

12. A process according to claim 9 wherein said working fluid is a compound or mixture of compounds that have a normal boiling point between about −100° C. to about 60° C.

13. A process according to claim 1 wherein said first heat recovery zone comprises a heat recovery device operated at a temperature of about −100° C. to about 60° C.

14. A process according to claim 13 wherein said second heat recovery zone comprises a heat recovery device operated at a temperature between about 80° C. to about 120° C.

15. A process according to claim 14 wherein said third heat recovery zone comprises a heat recovery device operated at a temperature between about 20° C. to about 100° C.

16. A process according to claim 15 wherein said first heat recovery zone comprises a partial condenser.

17. A process according to claim 16 wherein said second heat recovery zone comprises a heat recovery device selected from the group consisting of a condenser and a partial condenser.

18. A process according to claim 17 wherein said third heat recovery zone comprises a heat recovery device selected from the group consisting of a water cooler and an air cooler.

19. A process for recovery of thermal energy from an offgas streamsaid process comprising the following steps:
   a) oxidizing an aromatic feedstock with a liquid phase reaction mixture in a reaction zone to form an aromatic carboxylic acid stream and a gaseous mixture;
   b) removing in a separation zone a substantial portion of a solvent from said gaseous mixture to form said offgas stream and a solvent rich stream; and
   c) optionally, recovering thermal energy from a portion of said offgas stream in a first heat recovery zone to produce a low pressure steam;
   d) recovering thermal energy from a portion of said offgas stream in a second heat recovery zone using a working fluid in a power cycle comprising an organic rankine cycle or a kalina cycle; wherein said working fluid is a compound or mixture of compounds that have a normal boiling point between about −100° C. to about 90° C.;

e) optionally, recovering thermal energy from a portion of said offgas stream in a third heat recovery zone.

20. A process according to claim 19 wherein said first heat recovery zone comprises a heat recovery device operated at a temperature of about 100° C. to about 160° C.

21. A process according to claim 20 wherein said second heat recovery zone comprises a heat recovery device operated at a temperature between about 80° C. to about 120° C.

22. A process according to claim 21 wherein said third heat recovery zone comprises a heat recovery device operated at a temperature between about 20° C. to about 100° C.

23. A process according to claim 22 wherein said first heat recovery zone comprises a partial condenser.

24. A process according to claim 23 wherein said second heat recovery zone comprises a heat recovery device selected from the group consisting of a condenser and a partial condenser.

25. A process according to claim 24 wherein said third heat recovery zone comprises a heat recovery device selected from the group consisting of a water cooler and an air cooler.

26. A process according to claim 19 wherein said power cycle is an organic rankine cycle.

27. A process for recovery of thermal energy from an offgas stream said process comprising the following steps in the order named:
   a) oxidizing an aromatic feedstock with a liquid phase reaction mixture in a reaction zone to form an aromatic carboxylic acid stream and a gaseous mixture;
   b) removing in a separation zone a substantial portion of a solvent from said gaseous mixture to form said offgas stream and a solvent rich stream; and
   c) recovering thermal energy from a portion of said offgas stream in a first heat recovery zone to produce a low pressure steam;
   d) recovering thermal energy from a portion of said offgas stream in a second heat recovery zone using a working fluid in a power cycle comprising an organic rankine cycle or a kalina cycle; wherein said working fluid is a compound or mixture of compounds that have a normal boiling point between about −100° C. to about 90° C.; and
   e) recovering thermal energy from a portion of said offgas stream in a third heat recovery zone.

28. A process according to claim 27 wherein said first heat recovery zone comprises a heat recovery device operated at a temperature of about 100° C. to about 160° C.

29. A process according to claim 28 wherein said second heat recovery zone comprises a heat recovery device operated at a temperature between about 80° C. to about 120° C.

30. A process according to claim 29 wherein said third heat recovery zone comprises a heat recovery device operated at a temperature between about 20° C. to about 100° C.

31. A process according to claim 30 wherein said first heat recovery zone comprises a partial condenser.

32. A process according to claim 31 wherein said second heat zone comprises a heat recovery device is selected from the group consisting of a condenser and a partial condenser.

33. A process according to claim 32 wherein said third heat recovery zone comprises a heat recovery device is selected from the group consisting of a water cooler and an air cooler.

34. A process according to claim 27 wherein said power cycle is an organic rankine cycle.

* * * * *

UNITED STATES PATENT AND TRADEMARK OFFICE
CERTIFICATE OF CORRECTION

PATENT NO.         : 7,049,465 B2
APPLICATION NO.    : 10/617878
DATED              : May 23, 2006
INVENTOR(S)        : Lin

It is certified that error appears in the above-identified patent and that said Letters Patent is hereby corrected as shown below:

Correction(s)

Column 9, Line 59, Claim 9 "streamsaid" should read --stream said--;
Column 10, Line 52, Claim 19 "streamsaid" should read --stream said--;
Column 10, Line 56, Claim 19 "a substantial" should read --at least a --;
Column 11, Line 30, Claim 27 "a substantial" should read --at least a --.

Signed and Sealed this

Fifteenth Day of August, 2006

JON W. DUDAS
*Director of the United States Patent and Trademark Office*